US008101607B2

(12) United States Patent
Shuttleworth et al.

(10) Patent No.: US 8,101,607 B2
(45) Date of Patent: *Jan. 24, 2012

(54) PHARMACEUTICAL COMPOUNDS

(75) Inventors: Stephen J. Shuttleworth, Slough (GB); Adrian J. Folkes, Slough (GB); Irina S. Chuckowree, Slough (GB); Nan Chi Wan, Slough (GB); Timothy C. Hancox, Slough (GB); Stewart J. Baker, Slough (GB); Sukhjit Sohal, Slough (GB); Mohammed A. Latif, Slough (GB)

(73) Assignee: F. Hoffman-La Roche AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 12/835,533

(22) Filed: Jul. 13, 2010

(65) Prior Publication Data

US 2010/0280027 A1 Nov. 4, 2010

Related U.S. Application Data

(62) Division of application No. 11/665,657, filed as application No. PCT/GB2005/004137 on Oct. 25, 2005, now Pat. No. 7,776,856.

(30) Foreign Application Priority Data

Oct. 25, 2004 (GB) .................................. 0423653.5

(51) Int. Cl.
*A61K 31/5377* (2006.01)
(52) U.S. Cl. .................................................. 514/234.5
(58) Field of Classification Search ................ 514/234.5
See application file for complete search history.

(56) References Cited

U.S. PATENT DOCUMENTS

| 3,475,429 | A | 10/1969 | Woitun et al. |
| 3,661,908 | A | 5/1972 | Woitun et al. |
| 3,763,156 | A | 10/1973 | Woitun et al. |
| 3,838,121 | A | 9/1974 | Woitun et al. |
| 4,007,187 | A | 2/1977 | Fauran et al. |
| 4,146,716 | A | 3/1979 | Cox et al. |
| 4,196,207 | A | 4/1980 | Webber et al. |
| 6,187,777 | B1 | 2/2001 | Norman et al. |
| 6,608,053 | B2 | 8/2003 | Hayakawa et al. |
| 6,838,457 | B2 | 1/2005 | Hayakawa et al. |
| 7,037,915 | B2 | 5/2006 | Hayakawa et al. |
| 7,173,029 | B2 | 2/2007 | Hayakawa et al. |
| 7,776,856 | B2 | 8/2010 | Shuttleworth et al. |
| 2003/0220365 | A1 | 11/2003 | Stewart et al. |

FOREIGN PATENT DOCUMENTS

| EP | 1277738 A1 | 1/2003 |
| GB | 1393161 | 5/1975 |
| WO | WO 2004/017950 | 3/2004 |
| WO | WO 2004/065391 A1 | 8/2004 |
| WO | WO 2006/046031 A1 | 5/2006 |
| WO | WO 2006/046040 A1 | 5/2006 |

OTHER PUBLICATIONS

Cancer and Metastasis Reviews (1998), 17(1), 91-106.*
Science (1999), vol. 286, 531-537.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL;http://www.cnn.com/2003/HEALTH/conditions/09/24/alzheimers.drug.ap/index.html>.*
Huff, Joel R., "HIV Protease: A Novel Chemotherapeutic Target for AIDS," Journal of Medicinal Chemistry, vol. 34, No. 8, Aug. 1991, pp. 2305-2314.*
Bachman et al., "The *PIK3CA* gene is mutated with high frequency in human breast cancers", *Cancer Biology & Therapy*, 3(8), 772-775, Aug. 2004.
Berge et al., "Pharmaceutical Salts", *Journal of Pharmaceutical Sciences*, 66(1), 1-19, Jan. 1977.
Byrn et al., "Hydrates and Solvates", *Solid-State Chemistry of Drugs, Second Edition*, 233-247, 1999.
C. Garcia-Echeverria et al., "Drug discovery approaches targeting the PI3/Akt pathway in cancer", *Oncogene*, 27, 5511-5526, 2008.
Golub, T.R., et al., "Molecular Classification of Cancer: Class Discovery and Class Prediction by Gene Expression Monitoring", *Science*, 286, 531-537, (1999).
International Search Report for PCT/GB2005/004137 mailed Mar. 21, 2006.
Kang et al., "Phosphatidylinositol 3-kinase mutations identified in human cancer are oncogenic", *PNAS*, 102(3), 802-807, Jan. 18, 2005.
Lala, P.K. and A. Orucevic, "Role of nitric oxide in tumor progression: Lessons from experimental tumors", *Cancer and Metastasis Reviews*, 17(1), 91-106, (1998).
Liao, C., et al., "RO2492, a phosphoinositide-3-kinase δ inhibitor, shows inhibitory effects in a variety of human cell types and suppresses collagen-induced arthritis in mice", 74$^{th}$ Annual Scientific Meeting of the American College of Rheumatology, Atlanta, Nov. 6-11, 2010, *Arthritis Rheum.*, 62(10, Supp.), Abstract 288, (2010).
Manhas et al., "Heterocyclic Compounds. V. 2, 4-Disubstituted Thienopyrimidones (1)", *Journal of Heterocyclic Chemistry*, 13, 633-638, (1976).
Raynaud et al., "Biological properties of potent inhibitors of class I phophatidylinositide 3-kinases: from PI-103 through PI-540, PI-620 to the oral agent GDC-0941", *Mol. Cancer Ther.*, 8(7), 1725-1738, Jul. 2009.
Samuels et al., "High frequency of mutations of the *PIK3CA* gene in human cancers", *Science*, 304, 554, Apr. 23, 2004.

(Continued)

*Primary Examiner* — Rebecca Anderson
(74) *Attorney, Agent, or Firm* — Viksnis Harris & Padys PLLP

(57) ABSTRACT

Provided herein are methods of treating diseases or disorders arising from abnormal cell growth, function or behavior associated with PI3 kinase, which method includes administering to a patient in need thereof a compound that is a fused pyrimidine of formula (I):

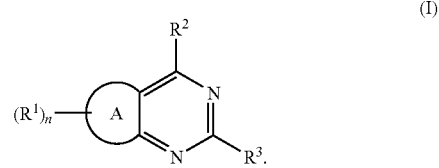

(I)

10 Claims, No Drawings

OTHER PUBLICATIONS

Shayesteh et al., "*PIK3CA* is implicated as an oncogene in ovarian cancer", *Nature Genetics*, 21, 99-102, Jan. 1999.

Workman et al., "Drugging the PI3 kinome", *Nature Biotechnology*, 24(7), 794-796, Jul. 2006.

Yap et al., "Targeting the PI3K-AKT-mTOR pathway: progress, pitfalls, and promises", *Current Opinion in Pharmacology*, 8, 393-412, 2008.

* cited by examiner

PHARMACEUTICAL COMPOUNDS

PRIORITY OF THE INVENTION

This application is a divisional of U.S. application Ser. No. 11/665,657, filed Jun. 6, 2007, which issued as U.S. Pat. No. 7,776,856 on Aug. 17, 2010, which is a 35 U.S.C. §371 U.S. filing of International Application Number PCT/GB2005/004137, filed Oct. 25, 2005, which claims priority to UK Application No. 0423653.5, filed Oct. 25, 2004, which applications are incorporated herein by reference.

FIELD OF THE INVENTION

The present invention relates to pyrimidine derivatives and their use as inhibitors of phosphatidylinositol 3-kinase (PI3K).

BACKGROUND TO THE INVENTION

Phosphatidylinositol (hereinafter abbreviated as "PI") is one of a number of phospholipids found in cell membranes. In recent years it has become clear that PI plays an important role in intracellular signal transduction. In the late 1980s, a PI3 kinase (PI3K) was found to be an enzyme which phosphorylates the 3-position of the inositol ring of phosphatidylinositol (D. Whitman et al, 1988, Nature, 332, 664).

PI3K was originally considered to be a single enzyme, but it has now been clarified that a plurality of subtypes are present in PI3K. Each subtype has its own mechanism for regulating activity. Three major classes of PI3Ks have been identified on the basis of their in vitro substrate specificity (B. Vanhaesebroeck, 1997, Trend in Biol. Sci, 22, 267). Substrates for class I PI3Ks are PI, PI 4-phosphate (PI4P) and PI 4,5-biphosphate (P1 (4,5)P2). Class I PI3Ks are further divided into two groups, class Ia and class Ib, in terms of their activation mechanism. Class Ia PI3Ks include PI3K p110α, p110β and p110δ subtypes, which transmit signals from tyrosine kinase-coupled receptors. Class Ib PI3K includes a p110γ subtype activated by a G protein-coupled receptor. PI and PI(4)P are known as substrates for class II PI3Ks. Class II PI3Ks include PI3K C2α, C2β and C2γ subtypes, which are characterized by containing C2 domains at the C terminus. The substrate for class III PI3Ks is PI only.

In the PI3K subtypes, the class Ia subtype has been most extensively investigated to date. The three subtypes of class Ia are heterodimers of a catalytic 110 kDa subunit and regulatory subunits of 85 kDa or 55 kDa. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Thus, the class Ia subtypes are considered to be associated with cell proliferation and carcinogenesis.

WO 01/083456 describes a series of condensed heteroaryl derivatives which have activity as inhibitors of PI3K and which suppress cancer cell growth.

SUMMARY OF THE INVENTION

It has now been found that a novel class of fused pyrimidine compounds are effective inhibitors of PI3K with drug-like physicochemical and pharmacokinetic properties. The compounds exhibit selectivity for class Ia PI3 Ks over class Ib, in particular for the P110δ subtype. Accordingly, the present invention provides a compound which is a fused pyrimidine of formula (I):

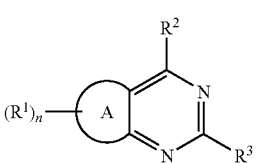

wherein
A represents a thiophene or furan ring;
n is 1 or 2;
$R^1$ is a group of formula:

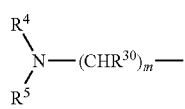

wherein
M is 0 or 1;
$R^{30}$ is H or $C_1$-$C_6$ alkyl;
$R^4$ and $R^5$ form, together with the N atom to which they are attached, a 5- or 6-membered saturated N-containing heterocyclic group which includes 0 or 1 additional heteroatoms selected from N, S and O, which may be fused to a benzene ring and which is unsubstituted or substituted; or one of $R^4$ and $R^5$ is alkyl and the other is a 5- or 6-membered saturated N-containing heterocyclic group as defined above or an alkyl group which is substituted by a 5- or 6-membered saturated N-containing heterocyclic group as defined above;
$R^2$ is selected from:

wherein $R^6$ and $R^7$ form, together with the nitrogen atom to which they are attached, a morpholine, thiomorpholine, piperidine, piperazine, oxazepane or thiazepane group which is unsubstituted or substituted; and

wherein Y is a $C_2$-$C_4$ alkylene chain which contains, between constituent carbon atoms of the chain and/or at one or both ends of the chain, 1 or 2 heteroatoms selected from O, N and S, and which is unsubstituted or substituted; and
$R^3$ is an indole group which is unsubstituted or substituted; or a pharmaceutically acceptable salt thereof.

DETAILED DESCRIPTION OF THE INVENTION

The thiophene or furan ring A in formula (I) adopts either of the two available regiochemical orientations. Formula (I)

thus covers the thieno[3,2-d]pyrimidines and furano[3,2-d] pyrimidines of the following formula (Ia) as well as the thieno [2,3-d]pyrimidines and furano[2,3-d]pyrimidines of the following formula (Ib):

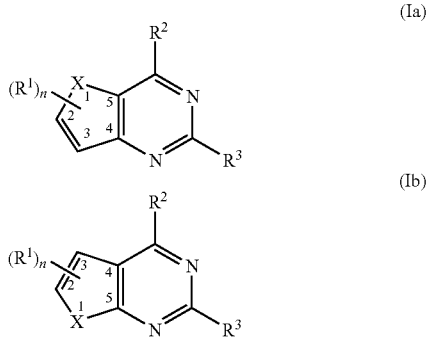

wherein each of $R^1$ to $R^3$ and n is as defined above and X is S or O.

In formula (I), the group or groups $R^1$, which are the same or different in a given compound when n is 2, may be bonded to either or both of the two available ring positions on the thiophene or furan ring A. Referring to structures (Ia) and (Ib) above, therefore, when n is 1 the furan or thiophene ring is mono-substituted by $R^1$ at the 2-position or the 3-position. When n is 2, the thiophene or furan ring is di-substituted by $R^1$ at positions 2 and 3.

As specified herein, an alkyl group is a straight or branched chain saturated hydrocarbon radical which is unsubstituted or substituted. Typically it is $C_1$-$C_{20}$ alkyl, for instance $C_1$-$C_{10}$ alkyl, such as $C_1$-$C_6$ alkyl or $C_1$-$C_4$ alkyl, for example methyl, ethyl, i-propyl, n-propyl, t-butyl, s-butyl or n-butyl. It may also be pentyl, hexyl, heptyl, octyl and the various branched chain isomers thereof.

When an alkyl group is substituted it typically bears one or more substituents $R^{20}$ selected from halogen, alkoxy, carbocyclyl, a 5- or 6-membered saturated N-containing heterocyclic group as defined above, OH, SR, CN, nitro, $NR_2$, —COOR, —C(O)R, —$CH_2$OR, $S(O)_m$R, —NRC(O)R, —$S(O)_m NR_2$, —OC(O)R, —$OC(O)NR_2$, —$NRS(O)_m$R, —$NRC(O)NR_2$ and —$CONR_2$, wherein each R is H, unsubstituted alkyl or $C_3$-$C_{10}$ cycloalkyl and m is 1 or 2.

Typically $R^{20}$ is selected from halogen, alkoxy, carbocyclyl, a 5- or 6-membered saturated N-containing heterocyclic group as defined above, OH, CN, $NR_2$, —COOR and —$CONR_2$, wherein each R is H or unsubstituted alkyl as defined above.

Substituted alkyl may be, for instance, a haloalkyl group or a group —alk-$N(R^4)(R^5)$ wherein alk is an alkylene chain and $R^4$ and $R^5$ form, together with the N atom to which they are attached, a 5- or 6-membered saturated N-containing heterocyclic group which includes 0 or 1 additional heteroatoms selected from N, S and O, which may be fused to a benzene ring and which is unsubstituted or substituted. More typically it is a haloalkyl group or a group —alk-$N(R^4)(R^5)$ wherein alk is an alkylene chain and $R^4$ and $R^5$ form, together with the N atom to which they are attached, a 5- or 6-membered saturated N-containing heterocyclic group as defined above.

An alkylene group is unsubstituted or substituted, straight or branched chain saturated divalent hydrocarbon group. Typically it is $C_1$-$C_8$ alkylene, for instance $C_1$-$C_6$ alkylene. Preferably it is $C_1$-$C_4$ alkylene, for example $C_2$-$C_4$ alkylene, such as methylene, ethylene, i-propylene, n-propylene, t-butylene, s-butylene or n-butylene. It may also be pentylene, hexylene, heptylene, octylene and the various branched chain isomers thereof. When the alkylene group is substituted it is typically substituted by a group $R^{20}$ as defined above or by alkyl which is unsubstituted or substituted by a group $R^{20}$ as defined above.

An alkenyl group is an unsubstituted or substituted, straight or branched chain hydrocarbon radical having one or more double bonds. Typically it is $C_2$-$C_8$ alkenyl, for instance $C_2$-$C_6$ alkenyl, such as allyl, butenyl, butadienyl, pentenyl or hexenyl. When the alkenyl group is substituted it is typically substituted by a group $R^{20}$ as defined above or by alkyl which is unsubstituted or substituted by a group $R^{20}$ as defined above.

An alkynyl group is an unsubstituted or substituted, straight or branched chain hydrocarbon radical having one or more triple bonds. Typically it is $C_2$-$C_8$ alkynyl, for instance $C_2$-$C_6$ alkynyl, such as ethynyl, propynyl or butynyl. When the alkynyl group is substituted it is typically substituted by a group $R^{20}$ as defined above or by alkyl which is unsubstituted or substituted by a group $R^{20}$ as defined above.

A haloalkyl group is an alkyl group as defined above, substituted by one or more halogen atoms. It can be a perhaloalkyl group, for instance trifluoromethyl or perfluorohexyl.

A halogen is chlorine, fluorine, bromine or iodine. It is typically bromine or iodine.

An alkoxy group is straight or branched chain. It is typically $C_1$-$C_6$ alkoxy, for instance $C_1$-$C_4$ alkoxy, such as methoxy, ethoxy, i-propoxy, n-propoxy, t-butoxy, n-butoxy or s-butoxy. It is unsubstituted or substituted, for instance by a group $R^{20}$ as defined above or by alkyl which is unsubstituted or substituted by a group $R^{20}$ as defined above. Typically it is substituted by carbocyclyl, morpholino, OH, CN, $NR_2$, —COOR or —$CONR_2$, wherein each R is H or unsubstituted alkyl as defined above.

A carbocyclyl group is a non-aromatic saturated or unsaturated monocyclic hydrocarbon ring, typically having from 3 to 10 carbon atoms. It may be a $C_3$-$C_8$ cycloalkyl group, or $C_5$-$C_{10}$ cycloalkyl group, for instance cyclopropyl, cyclobutyl, cyclopentyl, cyclohexyl, cycloheptyl or cyclooctyl. Alternatively it may be a cycloalkenyl group, typically $C_4$-$C_8$ cycloalkenyl, for instance cylcopentenyl, cyclohexenyl, cyclohexadienyl, cycloheptenyl, cyclohepadienyl, cyclooctenyl or cyclooctadienyl. A carbocyclyl group may be unsubstituted or substituted, for instance by a group $R^{20}$ as defined above or by alkyl which is unsubstituted or substituted by a group $R^{20}$ as defined above. Typically it is substituted by alkoxy, morpholino, OH, CN, $NR_2$, —COOR or —$CONR_2$, wherein each R is H or unsubstituted alkyl as defined above.

A 5- or 6-membered saturated N-containing heterocyclic group which includes 0 or 1 additional heteroatoms selected from N, S and O, which may be fused to a benzene ring and which is unsubstituted or substituted is typically selected from morpholine, piperidine, piperazine, pyrrolidine, thiomorpholine, quinoline, isoquinoline, diazepane, oxazepane and thiazepane.

When a 5- or 6-membered saturated N-containing heterocyclic group as defined above is substituted it may be substituted by a group $R^{20}$ as defined above or by alkyl which is unsubstituted or substituted by a group $R^{20}$ as defined above. Typically it is substituted by alkyl which is unsubstituted or substituted, alkoxy which is unsubstituted or substituted, a second 5- or 6-membered saturated N-containing heterocyclic group as defined above, a 5- or 6-membered N-containing heteroaryl group which is unsubstituted or substituted and which may be fused to a benzene ring, —NR'R", -alk-OR, —C(O)NR'R", -alk-C(O)NR'R", -alk-N(R)C(O)R, —C(O)N(R)-alk-OR, —$S(O)_2$-alk-NR'R", —N(R)-alk-OR, —COOR, oxo (=O), OR, —$N(R)SO_2$R, —$SO_2NR_2$, —$SO_2$R'" or —CO-alk-OR, wherein alk is an alkylene chain, R is H or alkyl, each of R' and R" is independently H, alkyl or alkoxy, or R' and R" together form a 5- or 6-membered saturated N-containing heterocyclic group as defined above, and R'" is alkyl which is unsubstituted or substituted, for instance by $NR_2$ or a 5- or 6-membered saturated N-containing heterocyclic group as defined above.

A 5-, 6- or 7-membered saturated heterocyclic group which contains 1 or 2 heteroatoms selected from N, S and O and which is unsubstituted or substituted is typically selected from tetrahydropyran, tetrahydrothiopyran, tetrahydrofuran and tetrahydrothiofuran.

When a 5-, 6- or 7-membered saturated heterocyclic group which contains 1 or 2 heteroatoms selected from N, S and O is substituted it may be substituted by a group $R^{20}$ as defined above or by alkyl which is unsubstituted or substituted by a group $R^{20}$ as defined above. Typically it is substituted by one or more substituents selected from alkyl which is unsubstituted or substituted, for instance by $R^{20}$ as defined above, haloalkyl as defined above, alkoxy as defined above which is unsubstituted or substituted, halogen, hydroxy, CN, nitro, amino, oxo (=O), and —NR'R" wherein each of R' and R" is independently H or alkyl.

A heteroaryl group is a heteroaryl group which contains 1, 2, 3 or 4 ring nitrogen atoms and 0, 1 or 2 additional heteroatoms selected from O, N and S, which group is monocyclic or bicyclic and which is unsubstituted or substituted. It is typically a 5- to 12-membered ring. Examples of a heteroaryl group include pyrrole, pyrazole, triazole, tetrazole, indazole, thiazole, isothiazole, oxazole, isooxazole, indole, isoindole, 1,3-dihydro-indol-2-one, pyridine-2-one, pyridine, pyridin-3-ol, imidazole, 1,3-dihydro-benzimidazolone, benzimidazole, benzothiazole, benzothiadiazole, quinoline, isoquinoline, quinoxaline, pyrazolopyridine, aminopyrazolinone, imidazopyridine, pyrimidine, pyridazine, pyrazine and isatin groups. Preferred examples include indazole, indole, pyrazole and tetrazole groups. These groups may be unsubstituted or substituted, for instance by a group $R^{20}$ as specified above or by alkyl which is unsubstituted or substituted by a group $R^{20}$ as defined above.

A 5- or 6-membered N containing heteroaryl group which may be fused to a benzene ring is typically selected from pyrrole, pyrazole, triazole, tetrazole, indazole, thiazole, isothiazole, oxazole, isooxazole, indole, isoindole, 1,3-dihydro-indol-2-one, pyridine-2-one, pyridine, pyridin-3-ol, imidazole, 1,3-dihydro-benzimidazolone, benzimidazole, benzothiazole, benzothiadiazole, quinoline, isoquinoline, quinoxaline, pyrazolopyridine, aminopyrazolinone, imidazopyridine, pyrimidine, pyridazine and pyrazine. When such a heteroaryl group is substituted it may be substituted by a group $R^{20}$ as defined above or by alkyl which is unsubstituted or substituted by a group $R^{20}$ as defined above.

In $R^1$, m is 0 or 1, typically 1. $R^{30}$ is typically H. $R^4$ and $R^5$ typically form, together with the N atom to which they are attached, a saturated N-containing heterocyclic group selected from morpholine, thiomorpholine, piperidine, piperazine, pyrrolidine, quinoline, isoquinoline, diazepane, oxazepane and thiazepane. The heterocyclic group formed by $R^4$ and $R^5$ is unsubstituted or substituted, for instance by the examples of substituent groups listed above, such as a group $R^{20}$ as defined above or by alkyl which is unsubstituted or substituted by a group $R^{20}$ as defined above.

In definition (a) of $R^2$ in formula (I), the ring formed by $R^6$ and $R^7$ is typically morpholine which is unsubstituted or substituted, for instance by a group $R^{20}$ as specified above or by alkyl which is unsubstituted or substituted by a group $R^{20}$ as specified above. It may alternatively be a group selected from tetrahydropyran, tetrahydrothiopyran, tetrahydrofuran and tetrahydrothiofuran, each of which is unsubstituted or substituted, for instance, for instance by a group $R^{20}$ as specified above or by alkyl which is unsubstituted or substituted by a group $R^{20}$ as defined above. When the ring formed by $R^6$ and $R^7$ is substituted it may be substituted on either a ring heteroatom or a ring carbon atom, for instance by a group $R^{20}$ as defined above or by alkyl which is unsubstituted or substituted by a group $R^{20}$ as defined above.

In definition (b) of $R^2$ in formula (I), the alkylene chain represented by Y forms, together with the carbon atoms to which it is attached, a saturated 5-, 6- or 7-membered heterocyclic ring which contains 1 or 2 heteroatoms selected from O, N and S and which is unsubstituted or substituted. Examples of the heterocyclic ring include tetrahydropyran, tetrahydrofuran, tetrahydrothiopyran, tetrahydrothiofuran and morpholine. When the heterocyclic ring is substituted it is typically substituted by one or more substituents, for instance 1, 2 or 3 substituents, selected from halogen, alkyl, haloalkyl (for instance trifluoromethyl), alkoxy, OH, CN, $NR_2$, oxo (=O), —COOR and —$CONR_2$, wherein each R is H or unsubstituted alkyl as defined above.

The indole group in the definition of $R^3$ is unsubstituted or substituted. If it is substituted it may be substituted by one or more substituents selected from a group Z, wherein Z is selected from selected from H, —OR, —SR, $CH_2OR$, —$CO_2R$, $CF_2OH$, $CH(CF_3)OH$, $C(CF_3)_2OH$, —$(CH_2)_qOR$, —$(CH_2)_qNR_2$, —$C(O)N(R)_2$, —$NR_2$, —$N(R)C(O)R$, —$S(O)_mN(R)_2$, —$OC(O)R$, $OC(O)N(R)_2$, —$N(R)S(O)_mR$, —$NRC(O)N(R)_2$, CN, halogen and —$NO_2$, wherein each R is independently selected from H, $C_1$-$C_6$ alkyl, $C_3$-$C_{10}$ cycloalkyl and a 5- to 12-membered aryl or heteroaryl group, the group being unsubstituted or substituted, m is 1 or 2 and q is 0, 1 or 2; one or more substituents selected from halo, alkyl, alkenyl, alkynyl, CN, $NO_2$, OR, SR, $NR_2$, C(O)R, SOR, $SO_2R$, $SO_2NR_2$, NRC(O)R and $CO_2R$, wherein each R is independently H or alkyl; and an oxo group (=O). Typically, if substituted, the indole group is substituted by OH, $NH_2$ or an oxo group. In one embodiment the indole group is unsubstituted.

The indole group $R^3$ is an isostere of a 3-hydroxyphenyl or 4-hydroxyphenyl group. An isostere as used herein is a functional group which possesses binding properties which are the same as, or similar to, the 3-hydroxyphenyl or 4-hydroxyphenyl group in the context of the structure of formula (I).

In one embodiment the pyrimidine is of formula (Ic):

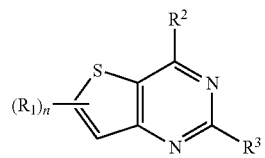

(Ic)

wherein
$R^2$ and $R^3$ are as defined above;
n is 1; and
$R^1$ is a group of formula

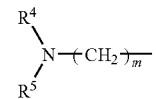

wherein
m is 0 or 1, and
$R^4$ and $R^5$ form, together with the N atom to which they are attached, a 5- or 6-membered saturated N-containing heterocyclic group which includes 0 or 1 additional heteroatoms selected from O, N and S and which is unsubstituted or substituted by alkyl, —$S(O)_2R$, —C(O)NR'R", -alk-C(O)NR'R", -alk-N(R)C(O)R, —C(O)N(R)-alk-OR, —$S(O)_2$-alk-NR'R", —N(R)-alk-OR, —$S(O)_2$-alk-NR'R", —N(R)-alk-OR and —C(O)-alk-OR wherein alk is an alkylene chain, R is H or alkyl and each of R' and R"

is independently H, alkyl or alkoxy, or R' and R" together form a 5- or 6-membered saturated N-containing heterocyclic group as defined above. Typically R' and R" together form a morpholine, piperidine or piperazine group, more typically a morpholine group.

In formula (Ic) the moiety "alk" is typically a straight-chain $C_1$-$C_4$ alkylene group, more typically $C_1$-$C_3$ alkylene, such as —$CH_2$—, —$CH_2CH_2$—, or —$CH_2CH_2CH_2$—. The heterocyclic group formed by $R^4$ and $R^5$ is typically selected from morpholine, piperidine and piperazine, each of which is unsubstituted or substituted as defined above. $R^2$ is typically morpholine. $R^3$ is typically an indole group which is unsubstituted.

Specific examples of compounds of the invention include:
2-(1H-Indol-4-yl)-6-(4-methyl-piperazin-1-ylmethyl)-4-morpholin-4-yl-thieno[3,2-d]pyrimidine;
2-(1H-Indol-4-yl)-6-(4-methanesulfonyl-piperazin-1-ylmethyl)-4-morpholin-4-yl-thieno[3,2-d]pyrimidine;
4-[2-(1H-Indol-4-yl)-4-morpholin-4-yl-thieno[3,2-d]pyrimidin-6-ylmethyl]-piperazine-1-carboxylic acid dimethylamide;
{4-[2-(1H-Indol-4-yl)-4-morpholin-4-yl-thieno[3,2-d]pyrimidin-6-ylmethyl]-piperazin-1-yl}-morpholin-4-yl-methanone;
4-[2-(1H-Indol-4-yl)-4-morpholin-4-yl-thieno[3,2-d]pyrimidin-6-ylmethyl]-piperazine-1-carboxylic acid (2-methoxy-ethyl)-methyl-amide;
{1-[2-(1H-Indol-4-yl)-4-morpholin-4-yl-thieno[3,2-d]pyrimidin-6-ylmethyl]-piperidin-4-yl}-(2-methoxy-ethyl)-methyl-amine;
2-(1H-Indol-4-yl)-4-morpholin-4-yl-6-piperazin-1-ylmethyl-thieno[3,2-d]pyrimidine;
2-(1H-Indol-4-yl)-4-morpholin-4-yl-6-(4-morpholin-4-yl-piperidin-1-ylmethyl)-thieno[3,2-d]pyrimidine;
2-{4-[2-(1H-Indol-4-yl)-4-morpholin-4-yl-thieno[3,2-d]pyrimidin-6-ylmethyl]-piperazin-1-yl}-ethanol;
{1-[2-(1H-Indol-4-yl)-4-morpholin-4-yl-thieno[3,2-d]pyrimidin-6-ylmethyl]-piperidin-4-yl}-dimethyl-amine;
4-((2-(1H-indol-4-yl)-4-morpholinothieno[3,2-d]pyrimidin-6-yl)methyl)-N-(2-methoxyethyl)-N-methylpiperazine-1-carboxamide; and
2-(4-((2-(1H-indol-4-yl)-4-morpholinothieno[3,2-d]pyrimidin-6-yl)methyl)piperazin-1-yl)-N,N-dimethylacetamide;
and the pharmaceutically acceptable salts thereof.

The compounds of formula (I) may exist in the form of geometrical isomers or tautomers depending on the kinds of substituent groups, and these isomers in separated forms or mixtures thereof may be used in the present invention. Where the compounds have asymmetric carbon atoms, optical isomer forms may exist based on such carbon atoms. All of the mixtures and the isolated forms of these optical isomers may be used in the present invention.

A suitable synthetic strategy for producing compounds of formula (I) in which m is 1 employs the precursor carboxaldehyde of formula (II):

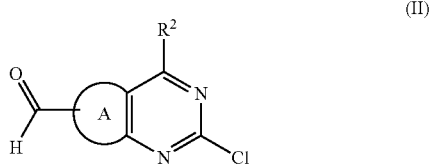

(II)

wherein A and $R^2$ are as defined above. Starting from this precursor the synthesis comprises performing, in either order, a palladium-mediated (Suzuki-type) cross-coupling reaction and a reductive amination. The present invention therefore further provides a process for producing a compound of formula (I) as defined above in which m is 1, which process comprises:

(a) treating a compound of formula (II):

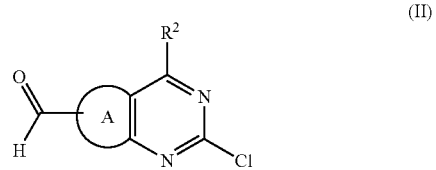

(II)

wherein A and $R^2$ are as defined above, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst; and treating the resulting compound of formula (III):

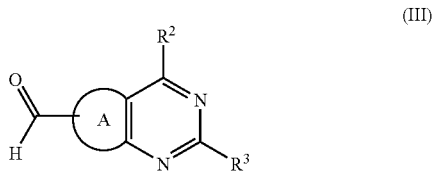

(III)

wherein A, $R^2$ and $R^3$ are as defined above, with an amine of formula $NHR^4R^5$ in which $R^4$ and $R^5$ are as defined above, in the presence of a suitable reducing agent; or (b) treating a compound of formula (II) as defined above with an amine of formula $NHR^4R^5$ wherein $R^4$ and $R^5$ are as defined above, in the presence of a suitable reducing agent; and treating the resulting compound of formula (IV):

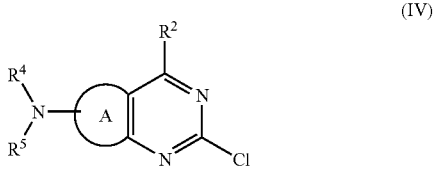

(IV)

wherein A, $R^2$, $R^4$ and $R^5$ are as defined above, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst.

Both the amination step and the Pd-mediated cross-coupling step take place under conventional conditions. The palladium catalyst may be any that is typically used for Suzuki-type cross-couplings, such as $PdCl_2(PPh_3)_2$. The reducing agent is typically a borohydride, for instance $NaBH(OAc)_3$, $NaBH_4$ or $NaCNBH_4$, in particular $NaBH(OAc)_3$.

A compound of formula (II) as defined above wherein $R^2$ is —$NR^6R^7$ may be prepared by a process which comprises treating a compound of formula (IX):

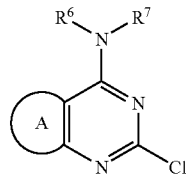

(IX)

wherein A, $R^6$ and $R^7$ are as defined above, with a lithiating agent followed by N,N'-dimethylformamide (DMF). The reaction is typically conducted by adding a solution of the lithiating agent in a non-polar organic solvent, for instance a hydrocarbon solvent such as hexane, to a suspension of the compound of formula (IX) in an organic solvent such as tetrahydrofuran (THF). If THF is used the addition takes place at a low temperature, of about −78° C. The lithiating agent is typically an alkyllithium, for instance n-butyllithium.

A compound of formula (IX) as defined above may be produced by a process which comprises treating a compound of formula (X):

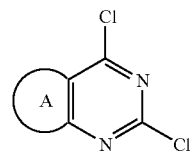

(X)

with an amine of formula $NHR^6R^7$, wherein $R^6$ and $R^7$ are as defined above, in an organic solvent. The solvent is typically an alcohol, such as methanol. The reaction is generally conducted at room temperature.

A compound of formula (X) may be prepared by the process described in Reference Example 1 for the preparation of 2,4-dichloro-thieno[3,2-d]pyrimidine, or by analogy with such a process.

A compound of formula (II) as defined above wherein $R^2$ is of formula

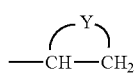

may be prepared by a process which comprises submitting a compound of formula (XI):

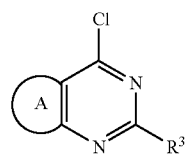

(XI)

wherein A and $R^3$ are as defined above, to palladium-mediated cross-coupling with a compound of formula (XII):

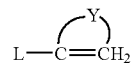

(XII)

wherein L is H or a group selected from halo, —$OSO_2CF_3$, —$B(OR)_2$, —$Sn(R)_3$ and —$Si(R)_3$ wherein R is H or alkyl as defined above, followed by reduction, to yield a compound of the following formula (XIII):

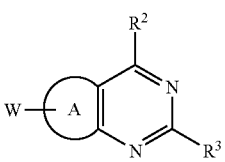

(XIII)

wherein A, $R^3$ and Y are as defined above.

The compound of formula (XIII) may be converted to the corresponding carboxaldehyde by treatment with a lithiating agent followed by N,N'-dimethylformamide (DMF), for instance under the conditions described above for the conversion of a compound of formula (IX) to a compound of formula (II). The lithiating agent is typically as defined above. The resulting carboxaldehyde may then be converted into a desired final compound of formula (I) as defined above, in which m is 1, by treatment with an amine of formula $NHR^4R^5$ in which $R^4$ and $R^5$ are as defined above, in the presence of a suitable reducing agent, for instance a borohydride as specified above, in particular $NaBH(OAc)_3$.

A compound of formula (I) as defined above in which m is 0 may be prepared by a Buchwald-type palladium-mediated nitrogen insertion reaction. Such a process may comprise treating a compound of formula (XIV):

(XIV)

wherein A, $R^2$ and $R^3$ are as defined above and W is a halo group selected from Br and I, with an amine of formula $NHR^4R^5$ in which $R^4$ and $R^5$ are as defined above, in the presence of a palladium catalyst.

A compound of formula (XIV) may be produced by treating a compound of formula (XV):

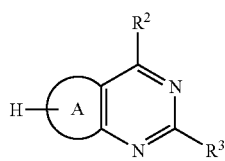

wherein A, $R^2$ and $R^3$ are as defined above, with a lithiating agent and a halogen selected from bromine and iodine. The lithiating agent is typically an alkyllithium, for instance butyllithium. The halogen is typically iodine, which gives rise to a compound of formula (XIV) in which W is I.

A compound of formula (I) as defined above in which m is 0 may also be prepared by an SNAr displacement reaction, for instance under the conditions described by D. Prim and G. Kirsch in Tetrahedron 55 (21), 6511-6526, 1999. Such a process comprises treating a compound of formula (XIV) as defined above in which W is Br with an amine of formula $NHR^4R^5$ in which $R^4$ and $R^5$ are as defined above in $H_2O$ under reflux for 12 hours.

A compound of formula (I) as defined above in which m is 0 may alternatively be prepared by treating a compound of formula (XIV) as defined above in which W is I with an amine of formula $NHR^4R^5$ in which $R^4$ and $R^5$ are as defined above in 1,4-dioxane in the presence of CuI/En and $K_3PO_4$. The reaction is conducted at about 110° C. for 24 hours. This procedure is described by Kang S-K et al in Synlett, (3), 427-430, 2002.

A fused pyrimidine of formula (I) may be converted into a pharmaceutically acceptable salt, and a salts may be converted into the free compound, by conventional methods. Examples of pharmaceutically acceptable salts include acid addition salts with inorganic acids such as hydrochloric acid, hydrobromic acid, hydroiodic acid, sulphuric acid, nitric acid and phosphoric acid; and organic acids such as formic acid, acetic acid, trifluoroacetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid and glutamic acid.

In the case of compounds of the invention bearing a free carboxy substituent, the salts include the salts of alkali and alkaline earth metals and ammonium, for instance the salts of sodium, potassium, magnesium, calcium and ammonium. The latter are prepared by treating the free fused pyrimidine of formula (I), or an acid addition salt thereof, with the corresponding metal base or ammonia. The compounds of formula (I) and their salts may exist as hydrates or solvates.

Compound of the present invention have been found in biological tests to be inhibitors of PI3 kinase. The compounds are selective for class Ia PI3 kinases over class Ib and typically exhibit at least a 20-fold selectivity for class Ia over class Ib PI3 kinases. In particular, the compounds are selective for the p110δ isoform over p110γ.

A compound of the present invention may thus be used as an inhibitor of PI3 kinase, in particular of a class Ia PI3 kinase. Accordingly, a compound of the present invention can be used to treat a disease or disorder arising from abnormal cell growth, function or behaviour associated with PI3 kinase. Examples of such diseases and disorders are discussed by Drees et al in Expert Opin. Ther. Patents (2004) 14(5):703-732. These include cancer, immune disorders, cardiovascular disease, viral infection, inflammation, metabolism/endocrine disorders and neurological disorders. Examples of metabolism/endocrine disorders include diabetes and obesity. Examples of cancers which the present compounds can be used to treat include leukaemia, brain tumours, renal cancer, gastric cancer and cancer of the skin, bladder, breast, uterus, lung, colon, prostate, ovary and pancreas.

A human or animal patient suffering from an immune disorder, cancer, cardiovascular disease, viral infection, inflammation, a metabolism/endocrine disorder or a neurological disorders may thus be treated by a method comprising the administration thereto of a compound of the present invention as defined above. The condition of the patient may thereby be improved or ameliorated.

In addition to possessing biochemical potency the compounds of the invention exhibit physicochemical and pharmacokinetic properties which make them particularly well adapted for drug use. This is shown for instance in the results of the biological assays described in Example 3, which follows. In particular the compounds possess high aqueous solubility at physiological pH; many have a solubility of at least 40 μm and a significant number have a solubility of greater than 100 μM. High solubility at physiological pH is desirable since it promotes bioavailability. The compounds also possess high metabolic stability, as shown in particular by the hepatocyte clearance assay described in Example 3 in which most of the tested compounds were shown to have low hepatocyte clearance. Low hepatocyte clearance correlates with a low rate of liver metabolism. It can therefore be seen that the compounds of the present invention possess improved physicochemical and pharmacokinetic properties whilst retaining biochemical potency as inhibitors of PI3 kinase.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection or infusion.

The dosage depends on a variety of factors including the age, weight and condition of the patient and the route of administration. Daily dosages can vary within wide limits and will be adjusted to the individual requirements in each particular case. Typically, however, the dosage adopted for each route of administration when a compound is administered alone to adult humans is 0.0001 to 50 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A compound is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. The compound may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents;

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

C) By inhalation, in the form of aerosols or solutions for nebulizers;

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols;

E) Topically, in the form of creams, ointments, jellies, collyriums, solutions or suspesions.

The invention will be further described in the Examples which follow:

REFERENCE EXAMPLE 1

2,4-dichloro-thieno[3,2-d]pyrimidine (64)

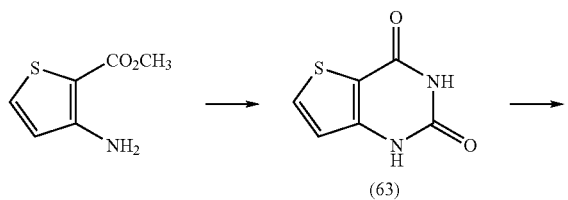
(63)

-continued

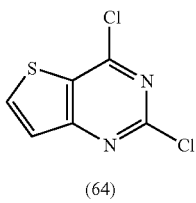

(64)

A mixture of methyl 3-amino-2-thiophenecarboxylate (13.48 g, 85.85 mmol) and urea (29.75 g, 5 eq.) was heated at 190° C. for 2 hours. The hot reaction mixture was then poured onto sodium hydroxide solution and any insoluble material removed by filtration. The mixture was then acidified (HCl, 2N) to yield 1H-thieno[3,2-d]pyrimidine-2,4-dione (63) as a white precipitate, which was collected by filtration and air dried (9.49 g, 66%).

$^1$H NMR (400 MHz, $d_6$-DMSO) 11.60-11.10 (2H, br, s), 8.10 (1H, d, J 5.2), 6.90 (1H, d, J 5.2).

A mixture of 1H-thieno[3,2-d]pyrimidine-2,4-dione (9.49 g, 56.49 mmol) and phosphorous oxychloride (150 mL) was heated at reflux for 6 hours. The reaction mixture was then cooled and poured onto ice/water with vigorous stirring yielding a precipitate. The mixture was then filtered to yield 2,4-dichloro-thieno[3,2-d]pyrimidine (64) as a white solid (8.68 g, 75%)

δH (400 MHz, CDCl$_3$) 8.13 (1H, d, J 5.5), 7.56 (1H, d, J 5.5).

REFERENCE EXAMPLE 2

2-Chloro-4-morpholin-4-yl-thieno[3,2-d]pyrimidine (65)

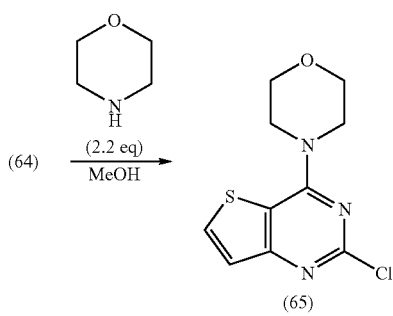

A mixture of 2,4-dichloro-thieno[3,2-d]pyrimidine (64), (8.68 g, 42.34 mmol), morpholine (8.11 mL, 2.2 eq.) and methanol (150 mL) was stirred at room temperature for 1 hour. The reaction mixture was then filtered, washed with water and methanol, to yield the title compound as a white solid (11.04 g, 100%).

$^1$H NMR (400 MHz, $d_6$-DMSO) 8.30 (1H, d, J 5.6), 7.40 (1H, d, J 5.6), 3.90 (4H, t, J 4.9), 3.74 (4H, t, J 4.9).

REFERENCE EXAMPLE 3

2-Chloro-4-morpholin-4-yl-thieno[3,2-d]pyrimidine-6-carbaldehyde (66)

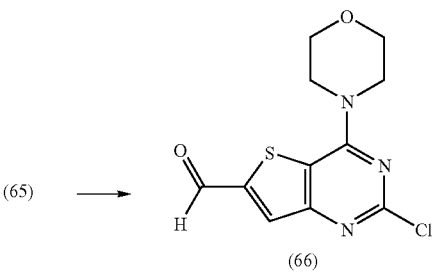

To a suspension of 2-chloro-4-morpholin-4-yl-thieno[3,2-d]pyrimidine (65) (1.75 g, 6.85 mmol) in dry tetrahydrofuran (40 mL) at −78° C. was added a 2.5M solution of nBuLi in hexane (3.3 mL, 1.2 eq.). After stirring for 1 hour, dry N,N-dimethylformamide (796 μL, 1.5 eq.) was added. The reaction mixture was stirred for 1 hour at −78° C. and then warmed slowly to room temperature. After a further 2 hours at room temperature the reaction mixture poured onto ice/water yielding a yellow precipitate. This was collected by filtration and air-dried to yield the title compound (1.50 g, 77%)

$^1$H NMR (400 MHz, $d_6$-DMSO) 10.20 (1H, s), 8.28 (1H, s), 3.95 (4H, t, J 4.9), 3.76 (4H, t, J 4.9).

REFERENCE EXAMPLE 4

2-chloro-6-(4-methyl-piperazin-1-yl-methyl)-4-morpholin-4-yl-thieno[3,2-d]pyrimidine (72)

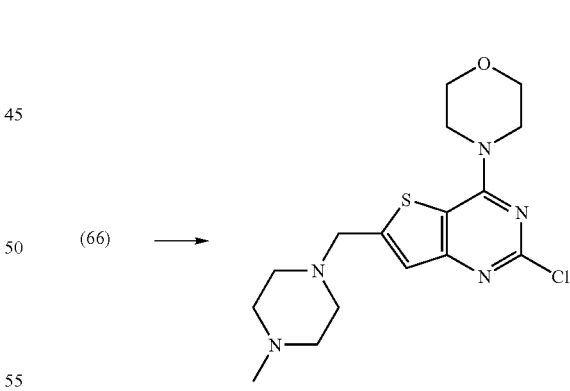

To a mixture of 2-chloro-4-morpholin-4-yl-thieno[3,2-d]pyrimidine-6-carbaldehyde (66) (147 mg, 0.52 mmol), 1-methyl-piperazine (1.5 eq., 87 μL) and acetic acid (1.05 eq., 32 μL) in 1,2-dichloroethane (3 mL) was added sodium triacetoxyborohydride (1.1 eq., 121 mg) and then stirred at room temperature overnight. The reaction mixture was diluted with dichloromethane, washed with a saturated solution of sodium hydrogen carbonate, brine, separated and dried (MgSO$_4$). The crude product was evaporated in vacuo and purified by chromatography to give the title compound 72 as an off-white crystalline solid (51 mg, 45%).

EXAMPLE 1

2-(1H-Indol-4-yl)-6-(4-methyl-piperazin-1-ylmethyl)-4-morpholin-4-yl-thieno[3,2-d]pyrimidine (61)

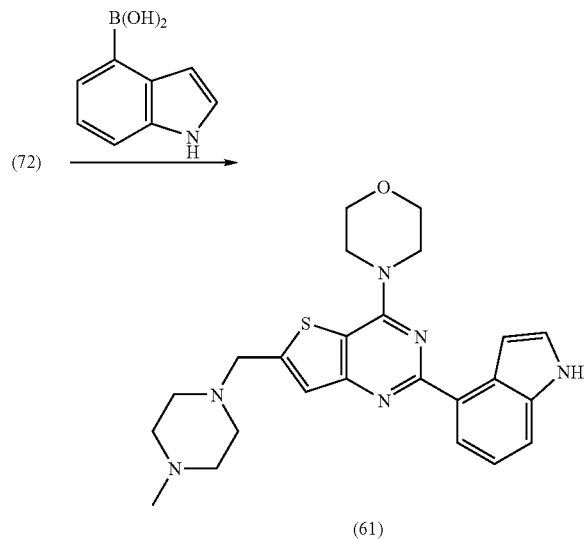

A mixture of 2-chloro-6-(4-methyl-piperazin-1-ylmethyl)-4-morpholin-4-yl-thieno[3,2-d]pyrimidine (72) (100 mg, 0.27 mmol), indole-4-boronic acid (1.1 eq., 48 mg), sodium hydrogen carbonate (3 eq., 69 mg) and bis(triphenylphosphine)palladium(II) chloride (0.05 eq., 10 mg) in toluene (2.5 mL), ethanol (1.5 mL) and water (0.7 mL) was flushed with argon and heated under microwave irradiation at 120° C. for 1 hour. The reaction mixture was partitioned between dichloromethane and water, organic layer was washed with brine, dried over magnesium sulfate, filtered and evaporated in vacuo. The resulting residue was purified using flash chromatography to yield the title compound 61 (23 mg, 19%).

$^1$H NMR (400 MHz, CDCl$_3$) 2.33 (s, 3H), 2.52 (brm, 4H), 2.63 (brm, 4H), 4.85 (s, 2H), 3.90-3.92 (m, 4H), 4.07-4.10 (m, 4H), 7.26-7.33 (m, 2H), 7.37 (s, 1H), 7.49 (d, 1H, J=8.0), 7.55 (m, 1H), 8.19 (d, 1H, J=7.3), 8.26 (brs, 1H).

MS (ESI$^+$) 449.1 (MH$^+$)

EXAMPLE 2

Further Compounds of the Invention

The following compounds of the invention were prepared by analogy with the process of Example 1. Compound 72 was replaced in each case by the appropriate precursor chloro compound, prepared by the method of Reference Example 4 using the relevant amine in place of 1-methyl piperazine. The preparation of the amine is described below where necessary. NMR data are given for each of the title compounds of the invention.

112: 2-(1H-Indol-4-yl)-6-(4-methanesulfonyl-piperazin-1-ylmethyl)-4-morpholin-4-yl-thieno[3,2-d]pyrimidine Via 2-Chloro-6-(4-methanesulfonyl-piperazin-1-ylmethyl)-4-morpholin-4-yl-thieno[3,2-d]pyrimidine, prepared from 1-methanesulfonyl-piperazine $^1$H NMR (400 MHz, CDCl$_3$): 2.67-2.71 (4H, m), 2.81 (3H, s), 3.29-3.33 (4H, m), 3.89 (2H, s), 3.89-3.93 (4H, m), 4.08-4.12 (4H, m), 7.28-7.33 (2H, m), 7.39 (1H, s), 7.50 (1H, d, J=8.2 Hz), 7.53-7.54 (1H, m), 8.19 (1H, d, J=8.0 Hz), 8.28 (1H, br s); MS (ESI$^+$) 513 (MH$^+$).

113: 4-[2-(1H-Indol-4-yl)-4-morpholin-4-yl-thieno[3,2-d]pyrimidin-6-ylmethyl]-piperazine-1-carboxylic acid dimethylamide Via 4-(2-Chloro-4-morpholin-4-yl-thieno[3,2-d]pyrimidin-6-ylmethyl)-piperazine-1-carboxylic acid dimethylamide, prepared from piperazine-1-carboxylic acid dimethylamide.

Amine preparation: to a solution of 1-BOC-piperazine (867 mg) in dry tetrahydrofuran (8 mL) was added triethylamine (0.97 mL) followed by dimethylcarbamoyl chloride (0.51 mL). After stirring for 24 hours the reaction mixture was then diluted with dichloromethane, washed with brine, dried (MgSO$_4$) and the solvent was removed in vacuo to yield 4-dimethylcarbamoyl-piperazine-1-carboxylic acid tert-butyl ester (940 mg). Treatment of this compound with HCl in dichloromethane/methanol yielded the compound 113.

$^1$H NMR (400 MHz, CDCl$_3$): 2.56-2.62 (4H, m), 2.83 (6H, s), 3.30-3.35 (4H, m), 3.87 (2H, s), 3.92-3.96 (4H, m), 4.08-4.12 (4H, m), 7.28-7.33 (2H, m), 7.38 (1H, s), 7.50 (1H, d, J=8.0 Hz), 7.56 (1H, s), 8.20 (1H, d, J=7.3 Hz), 8.30 (1H, br m);

MS (ESI$^+$) 506 (MH$^+$).

114: {4-[2-(1H-Indol-4-yl)-4-morpholin-4-yl-thieno[3,2-d]pyrimidin-6-ylmethyl]-piperazin-1-yl}-morpholin-4-yl-methanone Via [4-(2-Chloro-4-morpholin-4-yl-thieno[3,2-d]pyrimidin-6-ylmethyl)-piperazin-1-yl]-morpholin-4-yl-methanone, prepared from morpholin-4-yl-piperazin-1-yl-methanone;

$^1$H NMR (400 MHz, CDCl$_3$): 2.55-2.58 (4H, m), 3.28-3.32 (4H, m), 3.35-3.39 (4H, m), 3.67-3.71 (4H, m), 3.88 (2H, s), 3.92-3.96 (4H, m), 4.08-4.12 (4H, m), 7.28-7.33 (2H, m), 7.38 (1H, s), 7.50 (1H, d, J=8.0), 7.56 (1H, s), 8.20 (1H, d, J=7.3 Hz), 8.30 (1H, br m); (ESI+): MS (ESI$^+$) 548 (MH$^+$).

Amine preparation: A mixture of 4-morpholinocarbonyl chloride (0.38 ml), 1-BOC-piperazine (552 mg) and potassium carbonate (439 mg) in acetonitrile (7 mL) was stirred at room temperature for 3 hours. The reaction mixture was then diluted with dichloromethane, washed with brine, dried (MgSO$_4$) and the solvent removed in vacuo to yield 4-(morpholine-4-carbonyl)-piperazine-1-carboxylic acid tert-butyl ester (865 mg). Treatment of this compound with HCl in dichloromethane/methanol yielded the title compound, which was isolated as the hydrochloride salt.

115: 4-[2-(1H-Indol-4-yl)-4-morpholin-4-yl-thieno[3,2-d]pyrimidin-6-ylmethyl]-piperazine-1-carboxylic acid (2-methoxy-ethyl)-methyl-amide Via 4-(2-Chloro-4-morpholin-4-yl-thieno[3,2-d]pyrimidin-6-ylmethyl)-piperazine-1-carboxylic acid (2-methoxyethyl)-methyl-amide, prepared from piperazine-1-carboxylic acid (2-methoxy-ethyl)-methyl-amide Amine preparation: to N—BOC-piperazine (500 mg) in dichloromethane (5 mL) and triethylamine (0.41 ml) was added 4-nitrophenyl chloroformate (541 mg). After 1 hour the reaction mixture was diluted with dichloromethane, washed with brine, dried (MgSO$_4$) and the solvent was removed in vacuo to yield piperazine-1,4-dicarboxylic acid tert-butyl ester 4-nitro-phenyl ester (940 mg).

To piperazine-1,4-dicarboxylic acid tert-butyl ester 4-nitro-phenyl ester (500 mg) in tetrahydrofuran (5 mL) was added N-(2-methoxyethyl)methylamine (254 mg) and the reaction mixture was heated to reflux for 24 hours. The reaction mixture was reduced in vacuo and purified using flash chromatography to yield 4-[(2-methoxy-ethyl)methyl-carbamoyl]-piperazine-1-carboxylic acid tert-butyl ester (304 mg). Treatment of this compound with HCl in dichloromethane/methanol yielded the title compound, which was isolated as the hydrochloride salt.

$^1$H NMR (400 MHz, CDCl$_3$): 2.59-2.63 (4H, m), 2.90 (3H, s), 3.27-3.30 (4H, m), 3.31 (3H, s), 3.48 (2H, t), 3.57 (2H, t), 3.90 (2H, s), 3.92-3.96 (4H, m), 4.08-4.12 (4H, m), 7.28-7.33 (2H, m), 7.38 (1H, s), 7.50 (1H, d), 7.56 (1H, s), 8.20 (1H, d, J=7.3 Hz), 8.30 (1H, br m); MS (ESI$^+$) 550 (MH$^+$).

116: {1-[2-(1H-Indol-4-yl)-4-morpholin-4-yl-thieno[3,2-d]pyrimidin-6-ylmethyl]-piperidin-4-yl}-(2-methoxy-ethyl)-methyl-amine Via [1-(2-Chloro-4-morpholin-4-yl-thieno[3,2-d]pyrimidin-6-ylmethyl)-piperidin-4-yl]-(2-methoxy-ethyl)-methyl-amine, prepared from (2-methoxy-ethyl)-methyl-piperidin-4-yl-amine.

Amine preparation: a mixture of N-BOC-4-piperidine (500 mg), N-(2-methoxyethyl)methylamine (335 mg), acetic acid (0.15 mL) and sodium triacetoxyborohydride (797 mg) was stirred at room temperature in 1,2-dichloroethane (5 mL). After stirring overnight, the reaction mixture was diluted with chloroform, washed with sodium bicarbonate solution, dried (MgSO$_4$) and the solvent removed in vacuo. The residue was purified using flash chromatography to yield 4-[(2-methoxy-ethyl)-methyl-amino]-piperidine-1-carboxylic acid tert-butyl ester. Treatment of this compound with HCl in dichloromethane/methanol yielded the title compound, which was isolated as the hydrochloride salt.

$^1$H NMR (400 MHz, CDCl$_3$): 1.62-1.72 (2H, m), 1.76-1.84 (2H, m), 2.10-2.18 (2H, m), 2.36 (3H, s), 2.40-2.48 (1H, m), 2.68 (2H, t, J=6.0 Hz), 3.04-3.11 (2H, m), 3.38 (3H, s), 3.50 (2H, t, J=6.3 Hz), 3.85 (2H, s), 3.92-3.97 (4H, m), 4.08-4.12 (4H, m), 7.28-7.33 (2H, m), 7.38 (1H, s), 7.50 (1H, d, J=8.0 Hz), 7.56 (1H, s), 8.20 (1H, d, J=7.3 Hz), 8.30 (1H, br); MS (ESI$^+$) 521 (MH$^+$).

117: 2-(1H-Indol-4-yl)-4-morpholin-4-yl-6-piperazin-1-ylmethyl-thieno[3,2-d]pyrimidine Via ethereal HCl-mediated BOC-group cleavage of 4-[2-(1H-Indol-4-yl)-4-morpholin-4-yl-thieno[3,2-d]pyrimidin-6-ylmethyl]piperazine-1-carboxylic acid tert-butyl ester.

$^1$H NMR (400 MHz, d$_6$-DMSO): 2.90-3.05 (4H, br. m), 3.15-3.28 (4H, br. m), 3.86-3.92 (2H+4H, m), 4.18-4.25 (4H, br m), 7.05 (1H, br m), 7.30 (1H, t, J=7.8 Hz), 7.60 (1H, s), 7.72 (1H, d, J=8.1 Hz), 7.78 (1H, br s), 7.95 (1H, d, J=8.1 Hz), 9.30-9.40 (2H, br m), 11.60 (1H, br m); MS (ESI$^+$) 435 (MH$^+$).

118: 2-(1H-Indol-4-yl)-4-morpholin-4-yl-6-(4-morpholin-4-yl-piperidin-1-ylmethyl)-thieno[3,2-d]pyrimidine Via 2-Chloro-4-morpholin-4-yl-6-(4-morpholin-4-yl-piperidin-1-ylmethyl)-thieno[3,2-d]pyrimidine, prepared from 4-morpholinopiperidine (commercially available).

$^1$H NMR (400 MHz, CDCl$_3$): 1.55-1.68 (2H, m), 1.83-1.90 (2H, m), 2.11-2.18 (2H, m), 2.18-2.25 (1H, m), 2.54-2.60 (4H, m), 3.05-3.11 (2H, m), 3.70-3.76 (4H, m), 3.84 (2H, s), 3.92-3.96 (4H, m), 4.08-4.12 (4H, m), 7.28-7.33 (2H, m), 7.38 (1H, s), 7.50 (1H, d, J=8.0 Hz), 7.56 (1H, s), 8.20 (1H, d, J=7.3 Hz), 8.30 (1H, br); MS (ESI$^+$) 519 (MH$^+$).

119: 2-{4-[2-(1H-Indol-4-yl)-4-morpholin-4-yl-thieno[3,2-d]pyrimidin-6-ylmethyl]-piperazin-1-yl}-ethanol Via 2-[4-(2-Chloro-4-morpholin-4-yl-thieno[3,2-d]pyrimidin-6-ylmethyl)-piperazin-1-yl]-ethanol, prepared from N-(2-hydroxyethyl)piperazine (commercially available).

$^1$H NMR (400 MHz, CDCl$_3$): 2.63 (br m, 10H, 2×CH$_2$), 3.65 (m, 2H, CH$_2$), 3.84 (2H, s), 3.92-3.96 (4H, m), 4.08-4.12 (4H, m), 7.28-7.33 (2H, m), 7.38 (1H, s), 7.50 (1H, d, J=8.0 Hz), 7.56 (1H, s), 8.20 (1H, d, J=7.3 Hz), 8.30 (1H, br); MS (ESI$^+$) 479 (MH$^+$).

120: {1-[2-(1H-Indol-4-yl)-4-morpholin-4-yl-thieno[3,2-d]pyrimidin-6-ylmethyl]-piperidin-4-yl}-dimethyl-amine Via [1-(2-Chloro-4-morpholin-4-yl-thieno[3,2-d]pyrimidin-6-ylmethyl)-piperidin-4-yl]-dimethyl-amine, prepared from 4-dimethylaminopiperidne (commercially available).

$^1$H NMR (400 MHz, CDCl$_3$): 1.58-1.68 (2H, br m), 1.87-1.95 (2H, br m), 2.10 (2H, br t, J=10.7 Hz), 2.34 (1H, br m), 2.37 (6H, br s), 3.02 (2H, br m), 3.84 (2H, s), 3.92-3.96 (4H, m), 4.08-4.12 (4H, m), 7.28-7.33 (2H, m), 7.38 (1H, s), 7.50 (1H, d, J=8.0 Hz), 7.56 (1H, s), 8.20 (1H, d, J=7.3), 8.30 (1H, br m); MS (ESI$^+$) 477 (MH$^+$).

EXAMPLE 3

Biological Testing

Compounds of the invention, prepared as described in the preceding Examples, were submitted to the following series of biological assays (i) PI3K Biochemical Screening Compound inhibition of PI3K was determined in a radiometric assay using purified, recombinant enzyme and ATP at a concentration of 1 uM. All compounds were serially diluted in 100% DMSO. The kinase reaction was incubated for 1 hour at room temperature, and the reaction was terminated by the addition of PBS. IC$_{50}$ values were subsequently determined using sigmoidal dose-response curve fit (variable slope). All of the compounds exemplified had an IC$_{50}$ against PI3K of 510 uM or less. In particular, all of the compounds tested against the p110δ isoform of PI3K had an IC$_{50}$ of 0.1 μM or less.

(ii) Cellular Proliferation Inhibition

Cells were seeded at optimal density in a 96 well plate and incubated for 4 days in the presence of test compound. Alamar Blue™ was subsequently added to the assay medium, and cells were incubated for 6 hours before reading at 544 nm excitation, 590 nm emission. EC$_{50}$ values were calculated using a sigmoidal dose response curve fit. All the compounds tested had an $EC_{50}$s of 50 uM or less in the range of cell lines utilized.

(iii) Caco-2 Permeability

Caco-2 cells were seeded onto Millipore Multiscreen plates at $1\times10^5$ cells/cm², and were cultured for 20 days. Assessment of compound permeability was subsequently conducted. The compounds were applied to the apical surface (A) of cell monolayers and compound permeation into the basolateral (B) compartment was measured. This was performed in the reverse direction (B–A) to investigate active transport. A permeability coefficient value, $P_{app}$, for each compound, a measure of the rate of permeation of the compound across the membrane, was calculated. Compounds were grouped into low ($P_{app}$</=$1.0\times10^6$ cm/s) or high ($P_{app}$>/=$1.0\times10^6$ cm/s) absorption potential based on comparison with control compounds with established human absorption.

For assessment of a compound's ability to undergo active efflux, the ratio of basolateral (B) to apical (A) transport compared with A to B was determined. Values of B–A/A–B>/=1.0 indicated the occurrence of active cellular efflux. All of the compounds tested through the Caco-2 permeability screen had $P_{app}$ values>/=$1.0\times10^6$ cm/s. One compound assessed through the bidirectional assay, PI540, had an B–A/A–B asymmetry index of less than 1.0, indicating that the compound does not undergo active cellular efflux.

(iv) Hepatocyte Clearance

Suspensions of cryopreserved human hepatocytes were used. Incubations were performed at compound concentration of 1 mM or 4M at a cell density of $0.5\times10^6$ viable cells/mL. The final DMSO concentration in the incubation was 0.25%. Control incubations were also performed in the absence of cells to reveal any non-enzymatic degradation. Duplicate samples (50 μL) were removed from the incubation mixture at 0, 5, 10, 20, 40 and 60 minutes (control sample at 60 minutes only) and added to methanol—containing internal standard (100 μL)—to terminate the reaction. Tolbutamide, 7-hydroxycoumarin, and testosterone were used as control compounds. Samples were centrifuged and the supernatants at each time point pooled for analysis by LC-MSMS. From a plot of ln peak area ratio (parent compound peak area/internal standard peak area) against time, intrinsic clearance ($CL_{int}$) was calculated as follows: $CL_{int}$ (μl/min/million cells)=V×k, where k is the elimination rate constant, obtained from the gradient of ln concentration plotted against time; V is a volume term derived from the incubation volume and is expressed as uL $10^6$ cells$^{-1}$.

Compounds were classified with low (CL</=4.6 μL/min/$10^6$ cells), medium (CL>/=4.6; </=25.2 μl/min/$10^6$ cells) and high (>/=25.2 μl/min/$10^6$ cells) clearance. The majority of the tested compounds of the invention were determined to have low hepatocyte clearance.

(v) Cytochrome P450 Inhibition

Compounds of the invention were screened against five CYP450 targets (1A2, 2C9, 2C19, 2D6, 3A4) at 10 concentrations in duplicate, with a top concentration of 100 uM being used. Standard inhibitors (furafylline, sulfaphenazole, tranylcypromine, quinidine, ketoconazole) were used as controls. Plates were read using a BMG LabTechnologies PolarStar in fluorescence mode. The majority of the tested compounds assessed in this assay displayed weak activity ($IC_{50}$>/=5 uM) against all isoforms of CYP450.

(vi) Cytochrome P450 Induction

Freshly isolated human hepatocytes from a single donor were cultured for 48 hours prior to addition of test compound at three concentrations and were incubated for 72 hours. Probe substrates for CYP3A4 and CYP1A2 were added for 30 minutes and 1 hour before the end of the incubation. At 72 hours, cells and media were removed and the extent of metabolism of each probe substrate quantified by LC-MS/MS. The experiment was controlled by using inducers of the individual P450s incubated at one concentration in triplicate. The compounds of the invention assessed in this assay showed negligible effects on induction of cytochrome P450 enzymes.

(vii) Plasma Protein Binding

Solutions of test compound (5 um, 0.5% final DMSO concentration) were prepared in buffer and 10% plasma (v/v in buffer). A 96 well HT dialysis plate was assembled so that each well was divided in two by a semi-permeable cellulose membrane. The buffer solution was added to one side of the membrane and the plasma solution to the other side; incubations were then conducted at 37° C. over 2 hours in triplicate. The cells were subsequently emptied, and the solutions for each batch of compounds were combined into two groups (plasma-free and plasma-containing) then analysed by LC-MSMS using two sets of calibration standards for plasma-free (6 points) and plasma-containing solutions (7 points). The fraction unbound value for each compound was calculated: highly protein bound compounds (>/=90% bound) had an Fu</=0.1. The compounds of the invention assessed in this assay had Fu values>/=0.1.

(viii) hERG Channel Blockage

Compounds of the invention were evaluated for their ability to modulate rubidium efflux from HEK-294 cells stably expressing hERG potassium channels using established flux methodology. Cells were prepared in medium containing RbCl and were plated into 96-well plates and grown overnight to form monolayers. The efflux experiment was initiated by aspirating the media and washing each well with $3\times100$ μL of pre-incubation buffer (containing low $[K^+]$) at room temperature. Following the final aspiration, 50 μl of working stock (2×) compound was added to each well and incubated at room temperature for 10 minutes. 50 μL of stimulation buffer (containing high [K+]) was then added to each well giving the final test compound concentrations. Cell plates were then incubated at room temperature for a further 10 minutes. 80 μL of supernatant from each well was then transferred to equivalent wells of a 96-well plate and analysed via atomic emission spectroscopy. Compounds were screened as 10 pt duplicate $IC_{50}$ curves, n=2, from a top concentration of 100 μM.

EXAMPLE 4

Tablet Composition

Tablets, each weighing 0.15 g and containing 25 mg of a compound of the invention were manufactured as follows:

Composition for 10,000 tablets
Active compound (250 g)
Lactose (800 g)
Corn starch (415 g)
Talc powder (30 g)
Magnesium stearate (5 g)

The active compound, lactose and half of the corn starch were mixed.

The mixture was then forced through a sieve 0.5 mm mesh size. Corn starch (10 g) is suspended in warm water (90 ml). The resulting paste was used to granulate the powder. The granulate was dried and broken up into small fragments on a sieve of 1.4 mm mesh size. The remaining quantity of starch, talc and magnesium was added, carefully mixed and processed into tablets.

EXAMPLE 5

Injectable Formulation

Formulation A

| Active compound | 200 mg |
|---|---|
| Hydrochloric Acid Solution 0.1M or Sodium Hydroxide Solution 0.1M q.s. to pH | 4.0 to 7.0 |
| Sterile water q.s. to | 10 ml |

The compound of the invention was dissolved in most of the water (35° 40° C.) and the pH adjusted to between 4.0 and 7.0 with the hydrochloric acid or the sodium hydroxide as appropriate. The batch was then made up to volume with water and filtered through a sterile micropore filter into a sterile 10 ml amber glass vial (type 1) and sealed with sterile closures and overseals.

Formulation B

| Active Compound | 125 mg |
|---|---|
| Sterile, Pyrogen-free, pH 7 Phosphate Buffer, q.s. to | 25 ml |
| Active compound | 200 mg |
| Benzyl Alcohol | 0.10 g |
| Glycofurol 75 | 1.45 g |
| Water for injection q.s to | 3.00 ml |

The active compound was dissolved in the glycofurol. The benzyl alcohol was then added and dissolved, and water added to 3 ml. The mixture was then filtered through a sterile micropore filter and sealed in sterile 3 ml glass vials (type 1).

EXAMPLE 6

Syrup Formulation

| Active compound | 250 mg |
|---|---|
| Sorbitol Solution | 1.50 g |
| Glycerol | 2.00 g |
| Sodium benzoate | 0.005 g |
| Flavour | 0.0125 ml |
| Purified Water q.s. to | 5.00 ml |

The compound of the invention was dissolved in a mixture of the glycerol and most of the purified water. An aqueous solution of the sodium benzoate was then added to the solution, followed by addition of the sorbital solution and finally the flavour. The volume was made up with purified water and mixed well.

The invention claimed is:

1. A method of treating a disease or disorder arising from abnormal cell growth, function or behaviour associated with PI3 kinase, which method comprises administering to a patient in need thereof a compound which is a fused pyrimidine of formula (I):

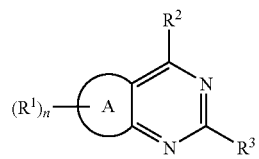

wherein

A represents a thiophene or furan ring;

n is 1 or 2;

$R^1$ is a group of formula:

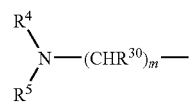

wherein m is 0 or 1;

$R^{30}$ is H or $C_1$-$C_6$ alkyl;

$R^4$ and $R^5$ form, together with the N atom to which they are attached, a 5- or 6-membered saturated N-containing heterocyclic group which includes 0 or 1 additional heteroatoms selected from N, S and O, which may be fused to a benzene ring and which is unsubstituted or substituted; or one of $R^4$ and $R^5$ is alkyl and the other is a 5- or 6-membered saturated N-containing heterocyclic group as defined above or an alkyl group which is substituted by a 5- or 6-membered saturated N-containing heterocyclic group as defined above;

$R^2$ is selected from:

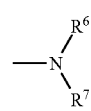

wherein $R^6$ and $R^7$ form, together with the nitrogen atom to which they are attached, a morpholine, thiomorpholine, piperidine, piperazine, oxazepane or thiazepane group which is unsubstituted or substituted; and

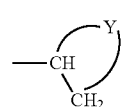

wherein Y is a $C_2$-$C_4$ alkylene chain which contains, between constituent carbon atoms of the chain and/or at one or both ends of the chain, 1 or 2 heteroatoms selected from O, N and S, and which is unsubstituted or substituted;

and $R^3$ is an indole group which is unsubstituted or substituted;

or a pharmaceutically acceptable salt thereof;

wherein the disease or disorder is inflammation.

2. The method of claim 1, wherein the fused pyrimidine is of formula (Ia):

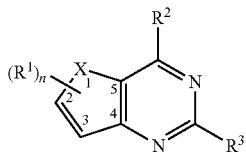

wherein X is S or O and R¹, R², R³ and n are as defined in claim 1.

3. The method of claim 1, wherein the fused pyrimidine is of formula (Ib):

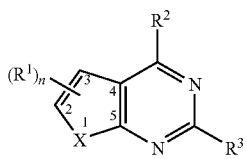

wherein X is S or O and R¹, R², R³ and n are as defined in claim 1.

4. The method of claim 1, wherein the fused pyrimidine is selected from:
- 2-(1H-Indol-4-yl)-6-(4-methyl-piperazin-1-ylmethyl)-4-morpholin-4-yl-thieno[3,2-d]pyrimidine;
- [2-(1H-Indol-4-yl)-6-(4-methanesulfonyl-piperazin-1-ylmethyl)-4-morpholin-4-yl-thieno[3,2-d]pyrimidine;
- 2-(1H-Indol-4-yl)-4-morpholin-4-yl-thieno[3,2-d]pyrimidin-6-ylmethyl]-piperazine-1-carboxylic acid dimethylamide;
- {4-[2-(1H-Indol-4-yl)-4-morpholin-4-yl-thieno[3,2-d]pyrimidin-6-ylmethyl]-piperazin-1-yl}-morpholin-4-yl-methanone;
- 4-[2-(1H-Indol-4-yl)-4-morpholin-4-yl-thieno[3,2-d]pyrimidin-6-ylmethyl]-piperazine-1-carboxylic acid (2-methoxy-ethyl)-methyl-amide;
- {1-[2-(1H-Indol-4-yl)-4-morpholin-4-yl-thieno[3,2-d]pyrimidin-6-ylmethyl]-piperidin-4-yl}-(2-methoxy-ethyl)-methyl-amine;
- 2-(1H-Indol-4-yl)-4-morpholin-4-yl-6-piperazin-1-ylmethyl-thieno[3,2-d]pyrimidine;
- 2-(1H-Indol-4-yl)-4-morpholin-4-yl-6-(4-morpholin-4-yl-piperidin-1-ylmethyl)-thieno[3,2-d]pyrimidine;
- 2-{4-[2-(1H-Indol-4-yl)-4-morpholin-4-yl-thieno[3,2-d]pyrimidin-6-ylmethyl]-piperazin-1-yl}-ethanol;
- {1-[2-(1H-Indol-4-yl)-4-morpholin-4-yl-thieno[3,2-d]pyrimidin-6-ylmethyl]-piperidin-4-yl}-dimethyl-amine;
- 4-((2-(1H-indol-4-yl)-4-morpholinothieno[3,2-d]pyrimidin-6-yl)methyl)-N-(2-methoxyethyl)-N-methylpiperazine-1-carboxamide; and
- 2-(4-((2-(1H-indol-4-yl)-4-morpholinothieno[3,2-d]pyrimidin-6-yl)methyl)piperazin-1-yl)-N,N-dimethylacetamide;

and the pharmaceutically acceptable salts thereof.

5. The method of claim 1, wherein the disease or disorder is associated with the class Ia subtype of PI3 kinase.

6. The method of claim 1, wherein the compound is administered orally or parenterally.

7. The method of claim 6, wherein the compound is administered orally.

8. The method of claim 6, wherein the compound is administered parenterally.

9. The method of claim 1, wherein the compound is administered intramuscularly, intravenously or subcutaneously.

10. The method of claim 1, wherein the compound is administered by injection or infusion.

* * * * *

UNITED STATES PATENT AND TRADEMARK OFFICE
CERTIFICATE OF CORRECTION

PATENT NO. : 8,101,607 B2
APPLICATION NO. : 12/835533
DATED : January 24, 2012
INVENTOR(S) : Shuttleworth et al.

Page 1 of 1

It is certified that error appears in the above-identified patent and that said Letters Patent is hereby corrected as shown below:

On the Title page in Item 74,

Replace:
Viksnis

With:
Viksnins

In the Claims,

In Column 24, in between lines 15 and 20, in the pictured figure,

Replace (due to printing error):
*m*

With:
m

In column 26, Line 5,

Replace:
carboxylic   acid

With:
carboxylic acid

Signed and Sealed this
Twenty-fourth Day of December, 2013

Margaret A. Focarino
*Commissioner for Patents of the United States Patent and Trademark Office*